United States Patent [19]

Dasgupta

[11] Patent Number: 5,766,959

[45] Date of Patent: Jun. 16, 1998

[54] METHOD FOR DETERMINING A COMPONENT USING A LIQUID FILM OR DROPLET

[75] Inventor: Purnendu K. Dasgupta, Lubbock, Tex.

[73] Assignee: The Dow Chemical Company, Midland, Mich.

[21] Appl. No.: 653,578

[22] Filed: May 24, 1996

[51] Int. Cl.$^6$ .................................................. G01N 1/00
[52] U.S. Cl. .................. 436/174; 436/164; 436/166; 436/167; 422/68.1; 422/58; 422/99; 422/100
[58] Field of Search .................................. 436/174, 177, 436/179, 180, 164, 165, 166, 167, 168, 805; 422/83, 88, 91, 99, 100, 68.1; 250/340, 341.1, 341.2, 573, 574, 576, 227.29

[56] References Cited

U.S. PATENT DOCUMENTS

| | | | |
|---|---|---|---|
| 4,659,677 | 4/1987 | Glover et al. | 436/174 |
| 4,910,402 | 3/1990 | McMillan | 250/341 |
| 5,004,913 | 4/1991 | Kleinerman | 250/227.21 |
| 5,558,837 | 9/1996 | Tsukishima | 422/99 |

OTHER PUBLICATIONS

*An Automated Imaging and Control System for the Continuous Determination of Size and Relative Mass of Single Compositionally Dynamic Droplets*, Maloney et al., Rev Sci Instrum 60(3), Mar. 1989, p. 450–455.

*Analytical Chemistry in a Liquid Film/Droplet*, A. Cardoso et al., Anal. Chem., 1995, vol. 67, 2562–6 Preliminary Investigation into the Analytical Potential of a Multiwavelength Fiber Drop.

*Analyzer with Special Reference to Applications in Medical Diagnostics*, McMillan et al., Optical Engineering, Dec. 1994, vol. 33, No. 12, pp. 3871–3890.

*Raman Scattering From Single Solution Droplets*, K. Hang Fung et al., Applied Optics, vol. 27, No. 2, Jan. 1988, pp. 206–208.

Liquid Droplet. A Renewable Gas Sampling Interface, S. Liu et al., Anal Chem, 1995, vol. 67, pp. 2042–2049.

*Model Development for Multicomponent Mass Transfer with Rapid Chemical Reactions in a Small Drop*, B.I. Noh et al., Korean J. of Cehm Eng 12(1), 18–22, 1995.

*Mass Transfer From A Single Micro–Droplet to a Gas Flowing at Low Reynolds Number*, Zhang et al., Chem Eng Comm 1987, vol. 50, pp. 51–67.

*Measurement of Gases by a Suppressed Conductometric Capillary Electrophoresis Separation System*, Dasgupta et al., Anal Chem 1995, 67, 3853–3860.

Measurement of phenols on a loop–supported liquid film by micellar electrokinetic chromatography and direct UV detection, P.K. Dasgupta, J. of Chromatography, pp.1–9, 1995.

*A Renewable Liquid Droplet as a Sampler and a Windowless Optical CEll. Automated Sensor for Gaseous Chlorine*, H. Liu et al., Analytical Chemistry, vol. 67 No. 23, 1995 pp. 4221–4228.

*Analytical Chemistry in a Drop. Solvent Extraction in a Microdrop*, H. Liu et al., Analytical Chemistry, American Chemical Society.

Primary Examiner—Long V. Le
Attorney, Agent, or Firm—Lisa T. Jozwiak

[57] ABSTRACT

A method for determining a component of interest in a fluid, the method comprising four steps. The first step is to suspend a droplet or a film of a liquid. The second step involves contacting the fluid with the droplet or film. The third step involves diffusing at least a portion of the component of interest into the droplet or film to form an analyte. The fourth step involves determining the component of interest by analyzing the analyte. The fluid can be either a liquid or a gas. The analyte can be analyzed while in the form of a suspended droplet or film.

10 Claims, 2 Drawing Sheets

5,766,959

1

METHOD FOR DETERMINING A COMPONENT USING A LIQUID FILM OR DROPLET

BACKGROUND OF THE INVENTION

Methods for sampling fluids are important in the area of analytical chemistry. In a gas stream, for example, it may be necessary to differentiate between the gases and any particles present in the gas phase. If the same component is present in both the gas and the particle, sampling becomes difficult.

Traditional methods of gas sampling include impingers or bubblers filled with a suitable solution and filters impregnated with suitable reagents. However, in using such samplers, the various collected gases can react with each other or with other particulate matter concurrently collected on the sampler. In some cases, the collected gases can volatilize during continued sampling.

Other traditional devices used for gas sampling include diffusion denuders, wet denuders, and membrane-based denuders. A diffusion denuder is a tube with its interior walls coated with substance that serves as an efficient sink for the desired gaseous component. A diffusion denuder can discriminate between gases and particles based on the large differences in the respective diffusion coefficients with an appropriate choice of the sampling rate and the length of the denuder tube, as the sample passes through the tube, the gas molecules diffuse quickly to the wall of the tube and are removed by the wall coating while most of the particles are transmitted. However, the analysis of the collected gas typically involves washing and collecting coating material followed by off-line measurement of the collected component of interest. Thus, the use of a diffusion denuder is tedious and labor intensive, requiring many discrete operations for a single measurement.

A wet denuder is a tube in which a suitable scrubber liquid flows down the inside walls and is aspirated off at the bottom while air is sampled in a countercurrent manner. However, there are components that cannot be easily concentrated from an aqueous matrix on a stationary phase. In such cases, enrichment factors greater than that attainable with a wet denuder may be desirable.

In a membrane-based denuder, also known as a diffusion scrubber (DS), a scrubber liquid flows through a membrane tube and air is sampled outside it. This device produces a continuous liquid effluent that can be coupled to continuous or semicontinuous liquid phase analyzers. However, the collection efficiencies of DS devices are typically low and membranes are susceptible to fouling.

The world of analytical chemistry increasingly involves smaller scales and miniature devices. It would be an advance in the art of sampling if an efficient method of sampling were available that could easily apply to the small scales of increasing importance in analytical chemistry.

SUMMARY OF THE INVENTION

The instant invention solves the above mentioned problem of inefficient sampling in analytical chemistry to a large degree. A liquid drop may not only the classic advantages of diffusive collection, but also, since such a droplet is readily renewable, there should be no fouling problems as with membranes.

The instant invention is a method for determining a component of interest in a fluid, the method comprising four steps. The first step is to suspend a droplet of a liquid. The second step involves contacting the fluid with the droplet. The third step involves diffusing at least a portion of the component of interest into the droplet to form an analyte. The fourth step involves determining the component of interest by analyzing the analyte.

The instant invention is also a method for determining a component of interest in a fluid, the method comprising four steps. The first step involves suspending a film of a liquid. The second step involves contacting the fluid with the film. The third step involves diffusing at least a portion of the component of interest into the film to form an analyte. The fourth step involves determining the component of interest by analyzing the analyte.

The fluid can be either a liquid or a gas. The analyte can be analyzed while in the form of a suspended droplet or film.

DETAILED DESCRIPTION OF THE INVENTION

The method of the instant invention will be described with respect to embodiments of apparatus which can be used to practice the method in a laboratory.

Figure 1:
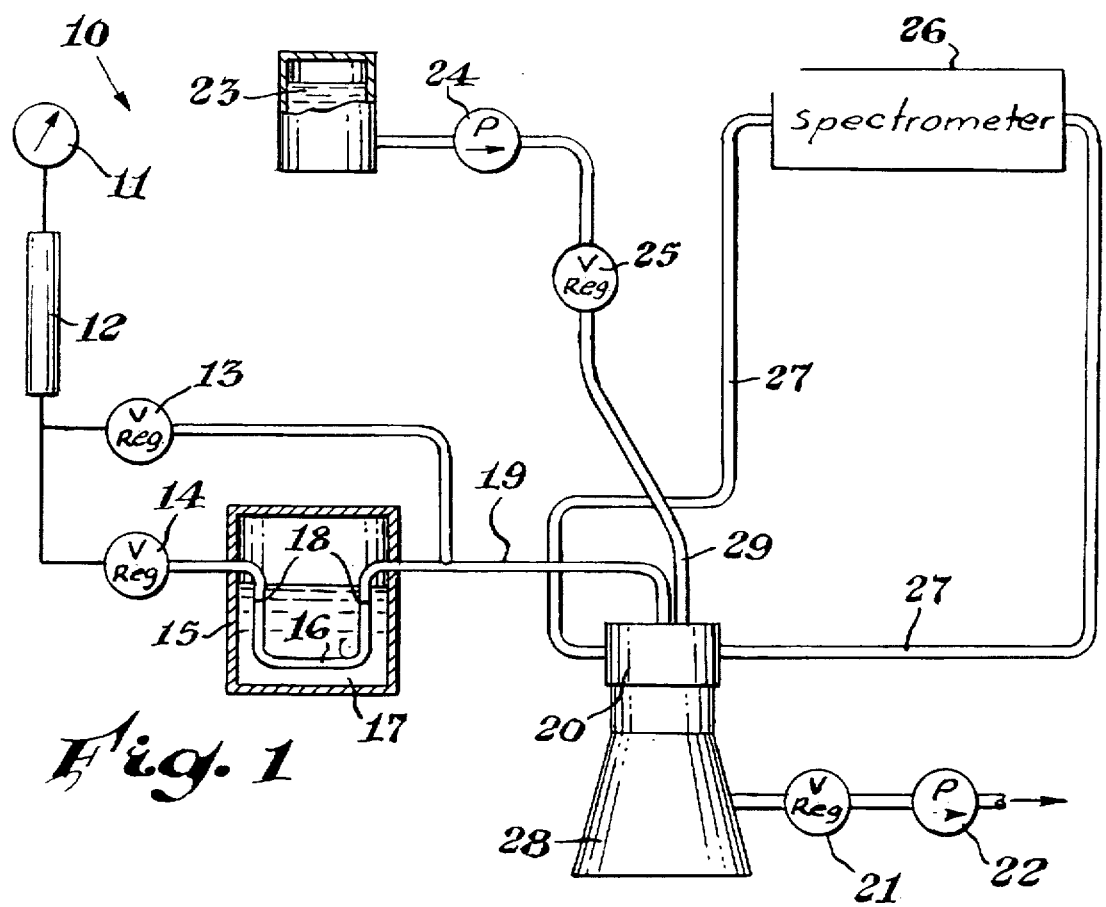
FIG. 1 shows an apparatus that can be used to practice the instant invention.

Referring now to FIG. 1, therein is shown a schematic diagram of an apparatus 10 that can be used to practice the method of the instant invention. A pressure regulator 11 regulates air flowing through the apparatus 10. The air flows through a filter 12 and then through either of two flow controllers 13 or 14. The air that flows through flow controller 14 flows through a permeation tube chamber 15, wherein at least one component of interest enters the air, resulting in a fluid 19. The fluid 19 flows through conduit 29 to a collection/analysis chamber 20, wherein the fluid 19 contacts a suspended droplet or film. The collection/analysis chamber 20 is attached to a flask 28. The flow of fluid through the collection/analysis chamber 20 is adjusted using a flow controller 21 and an aspiration pump 22.

Meanwhile, a pump 24 transports a collection reagent 23 through a flow controller 25 and into the collection/analysis chamber 20, where the collection reagent 23 forms the droplet or film that is suspended inside the collection/analysis chamber 20. As the fluid 19 moves past the suspended droplet or film inside the collection/analysis chamber 20, the component of interest diffuses from the fluid 19 into the suspended roplet or film, thereby forming an analyte. The nalyte can then be analyzed using, for example, spectrometer 26 and optical fibers 27.

The source of air that is measured by pressure gauge 11 can be bottled air or compressed air, or any other convenient source of air. The air flows through filter 12, which is a column of activated carbon, silica gel and soda lime for air purification (MiniCapsule filter, 0.2 microns, P/N 12122, Gelman Sciences Inc., Ann Arbor, Mich.). The air flows through either flow controller 13 or flow controller 14 (Model FC-280, Tylan General, Torrance, Calif.). Tubing, such as stainless steel tubing or teflon tubing, connects the various elements of apparatus 10.

It should be understood that air is only one example of a carrier fluid. The carrier fluid can be any other gas or a liquid. The appropriate carrier fluid will depend upon various factors, including the component of interest, the reactivity of the materials used, and the availability of an appropriate collection reagent.

The air that flows through flow controller 14 passes to permeation tube chamber 15. The permeation tube chamber 15 contains a tube 16 that is made of a porous material, such as porous TEFLON (sixty centimeters by 5.5 millimeter inside diameter, Accurel, V8/2 mean pore size 0.2 microns, Akzo Inc., Wuppertal, Germany). The tube 16 is connected to the tubing surrounding the permeation tube chamber 15 by tubing connectors 18. The permeation tube chamber 15 also a generation solution 17 containing a component of interest.

Inside the permeation tube chamber 15, the component of interest is transported from generation solution 17 into the air through pores in tube 16. At a constant temperature and a relatively low flow rate of air, equilibrium is established. The result is a fluid 19 that contains a component of interest. The term "fluid" is defined herein and in the claims to mean either a gas or a liquid which contains at least one component of interest to be analyzed. If desired, the fluid can be pure air or pure water, in which case the concentration of the component of interest would be zero. Pure air or pure water can be useful to establish a baseline.

It should be understood that the embodiment of FIG. 1 is for test purposes in a laboratory. The instant invention can also be used for other applications, such as directly on-line in a process. When the present invention is used on-line, of course, the sample gas will contain a component of interest without having to pass through a permeation chamber.

As the fluid 19 leaves the permeation tube chamber 15, the concentration of the component of interest in the air can be adjusted if necessary, by adjusting the flow rate of pure air flowing through flow controller 13.

The fluid 19 then flows to the collection/analysis chamber 20. Inside the collection/analysis chamber 20, the fluid 19 contacts a liquid droplet or film that is suspended inside the collection/analysis chamber 20. The flow rate of the fluid to the collection/analysis chamber 20 is controlled by flow controller 21 and aspiration pump 22. The collection/analysis chamber 20 will be described in more detail below, in reference to FIGS. 2 and 3.

The suspended droplet or film inside the collection/analysis chamber 20 is formed from the collection reagent 23. The collection reagent 23 is preferably a liquid that will absorb the component of interest. For example, a chromogenic reagent can be used. In particular, if nitrogen dioxide is the component of interest, Griess-Saltzman reagent can be a useful collection reagent. The collection reagent 23 is pumped into the collection/analysis chamber 20 at a sufficient rate to form a droplet or a film inside the chamber 20. Pump 24 and flow controller 25 are used to control the size of the droplet or film. The flow of the liquid delivered by pump 24 can be continuous or intermittent. Alternatively, the collection reagent 23 can be gravity fed to the collection/analysis chamber 20.

As the fluid flows past the droplet or film inside the collection/analysis chamber 20, the component of interest diffuses from the fluid into the droplet or film, forming an analyte. The term "analyte" is defined herein and in the claims to mean a material which is to be analyzed for a component of interest. The component of interest can be merely dissolved in the collector droplet/film, or the component of interest can react with one or more reagents in the collector droplet/film, thereby forming a different compound that is more amenable to measurement. The analyte can be determined either in-situ, meaning inside the collection/analysis chamber, or the analyte can be analyzed after transfer to a conjoined or separate analysis system. The analyte can be analyzed using, for example, a spectrometer 26. The analyte is preferably analyzed directly in the collection analysis/chamber 20, while in the form of a suspended droplet or film, using optical fibers 27 placed on opposite sides of and in close proximity to the droplet or film. One optical fiber 27 transmits light across the droplet or film while the other detects the amount of light that passes through the droplet or film. In an alternative embodiment, the droplet/film is excited by light from an optical fiber placed within the droplet/film and the resulting fluorescence is measured by a photodetector surrounding the droplet/film.

The absorbance is analyzed using the spectrometer 26. However, electrochemical methods can also be used to analyze the analyte. Alternatively, the analyte can also be aspirated, or drawn back out of the collection/analysis chamber 20, and analyzed elsewhere. Thus, in this alternative, various analytical methods may be used to determine the component of interest, including mass spectroscopy, chromatography and electrophoresis.

Figure 2:
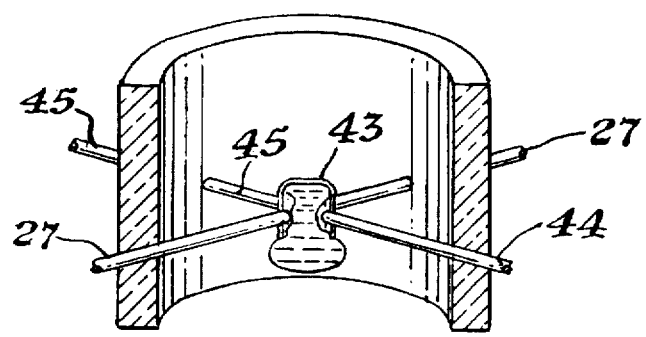
FIG. 2 shows a portion of the apparatus shown in FIG. 1.

Referring now to FIG. 2, therein is shown an embodiment of the collection/analysis chamber 20. The chamber housing 42 is a nine millimeter diameter PLEXIGLASS tube, although any other appropriate material, such as TEFLON or stainless steel, can be used. Cross-holes are drilled into the housing 42, so that reagent supply tubing 44 and support tubing 45 can extend through the housing 42 and be held in place using nuts and ferrules.

A wire guide 43, shaped like an inverted U, is made from 0.25 millimeter diameter platinum wire, three millimeters in width and five millimeters in height. The wire guide 43 is positioned at about a forty-five degree angle with respect to the tubes 44 and 45, with its top just protruding beyond the top perimeter of tubes 44 and 45. Support tube 45 is adjusted to hold the wire 43 snug in place. Collection reagent 23 is fed through the reagent supply tube 44 to form a film 41 on the wire 43.

As fluid 19 moves past the film 41 inside the collection/analysis chamber 20, a component of interest diffuses from the fluid 19 into the film 41, forming an analyte. The analyte can then be analyzed using, for example, fiber optics and a spectrometer 26. In this regard, silica optical fibers 27, one millimeter in diameter, are positioned at right angles to the tubes 44 and 45 and are held in place by nuts. One fiber 27 transmits light, while the other fiber 27 detects the transmitted light and sends a signal to the spectrometer to be analyzed.

Figure 4:
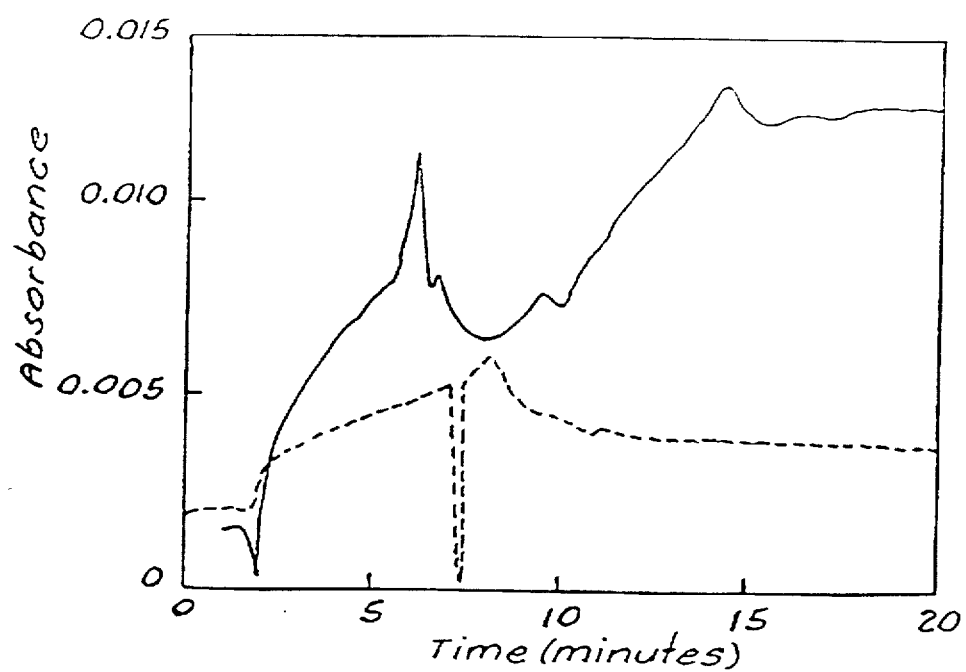
FIG. 4 shows a graph generated using the instant invention.

Referring now to FIG. 4, therein is shown an example of graph that results using the apparatus shown in FIGS. 1 and 2. The graph represents the absorbance of light by a suspended film as it is contacted with a fluid containing nitrogen dioxide as a component of interest. The solid line represents the absorbance for a fluid having a nitrogen dioxide ($NO_2$) concentration of 260 parts per billion by volume. The peak concentration of $NO_2$ in the film is reached after about fifteen minutes. The dotted line represents the absorbance for a fluid having an $NO_2$ concentration of thirty-one parts per billion by volume. The peak concentration of $NO_2$ is reached after about eight minutes. It should be understood that FIG. 4 is only one example of a graph that can result using the instant invention. The particular graph that results from a particular analysis will depend upon various factors, such as the concentration of the component of interest in the fluid, the duration of sampling time, the flow rate of the fluid past the droplet or film, and the relative humidity.

Figure 3:
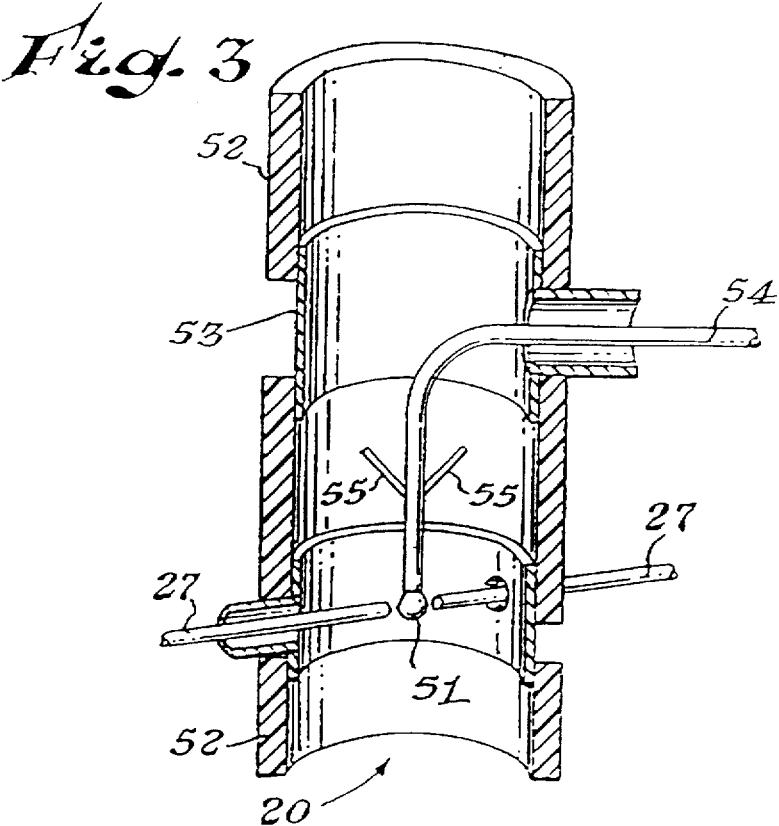
FIG. 3 shows a portion of the apparatus shown in FIG. 1.

Referring now to FIG. 3, therein is shown an alternative embodiment of the collection/analysis chamber 20. The housing 52 is TEFLON, although any other appropriate material, such as PLEXIGLASS or stainless steel, can be used. A reagent supply capillary 54 enters the collection/analysis chamber 20 through a polypropylene tee 53. The capillary is supported by supports 55 inside the collection/analysis chamber 20.

Collection reagent 23 is fed through the reagent supply capillary 54 to form a droplet 51 suspended at the tip of the capillary 54. The term "suspended" is defined herein and in the claims to mean that the droplet or film hangs from a support. The support can be, for example, a capillary or a wire. The size of the droplet is controlled by reagent pumping time so that various sizes of droplets can be used. The droplet can be static during sampling or the droplet can be continuously growing while it is suspended and then fall so that the droplet is no longer suspended.

As fluid 19 moves past the droplet 51 inside the collection/analysis chamber 20, at least one component of interest diffuses from the fluid 19 into the droplet 51, forming an analyte. In this regard, a liquid drop may not only provide the classic advantages of diffusive collection, but also, since such a droplet is readily renewable, there should be no fouling problems as with membranes. Furthermore, the diffusive flux of molecules that evaporate from the drop constitute an effective barrier to the approach of particles. This is known in the literature as "diffusiophoresis". See, e.g., Hinds, W. C., Aerosol Technology, Wiley, N.Y., p. 161 (1982).

The analyte can then be analyzed using, for example, fiber optics and a spectrometer 26. In this regard, silica optical fibers 27, one millimeter in diameter, can be positioned in the chamber 20 using polypropylene connectors 56. One fiber 27 brings in incident light which is transmitted through the droplet 51, while the other fiber 27 detects the transmitted light and sends a signal to the spectrometer to be analyzed. Alternatively, the analyte can be aspirated back through the capillary 54 and analyzed outside of the chamber.

It should be understood that the shape of the drop need not be spherical. An elliptical droplet or a film can be used.

The relative humidity (RH) of the fluid 19 can have two different effects on the amount of the component of interest collected. The first is the effect on the evaporative loss of water from the droplet, which can be substantial, especially at low RH values and for long sampling periods. The RH of the fluid can also affect the collection efficiency, which might decrease with increasing RH, due, for example, to formation of ammonia hydrates, $NH_3(H_2O)n$, in the gas phase during the sampling of ammonia.

It is interesting to note that sample RH information is available from the sampling system. If a given size drop is formed and fluid sampling then carried out at a fixed flow rate for a fixed period of time, the final size of the drop decreases with decreasing sample RH and can be used to determine sample RH. Similarly, in a system where a drop continuously forms and falls, the drop always detaches when a certain mass has accumulated. If there is a constant flow into the drop, the drop interval increases with decreasing RH due to evaporative loss and can be used to determine RH.

It should be understood, that, while the apparatus in FIGS. 1, 2 and 3 relate to gas measurement, the instant invention can extend to liquid measurement. In this regard, the fluid 19 can be a liquid that does not readily dissolve in the droplet/film. Using an annular drop head, it is possible to form one liquid film on top of an immiscible liquid drop. More detail about the apparatus used to practice the instant invention can be found in the inventor's publications in *Analytical Chemistry*, which are herein fully incorporated by reference. A. Cardoso & P. Dasgupta, "Analytical Chemistry in a Liquid Film/Droplet," Anal. Chem., 1995, vol. 67, 2562–2566; S. Liu and P. Dasgupta, "Liquid Droplet. A Renewable Gas Sampling Interface," Anal. Chem., 1995, vol. 67, 2042–2049; H. Liu and P. K. Dasgupta, "A Renewable Droplet as a Sampler and a Windowless Optical Cell. Automated Sensor for Gaseous Chlorine," Anal. Chem. 1995, 67, 4221–28.

EXAMPLE 1

The apparatus shown in FIGS. 1 and 2 is used to practice the instant invention. The collection reagent 23 is a Griess-Saltzman reagent comprising anhydrous sulfanilic acid, glacial acetic acid, and N-1-(napthyl) ethylene-diamine dihydrochloride. A liquid film is formed by gravity-feeding the collection reagent through the reagent supply tube 44 at a rate of 2.4 microliters per second until a film having a volume of about fourteen microliters is formed.

The permeation tube chamber contains a permeation tube that emits seventy nanograms of nitrogen dioxide ($NO_2$) per minute (VICI Metronics, Santa Clara, Calif.). The resulting fluid is air that contains 260 parts per billion by volume (ppbv) $NO_2$ as the component of interest. The fluid is fed to the collection/analysis chamber so that the fluid contacts the suspended film at a flow rate of about 0.13 liters per minute.

Light from a high intensity green light emitting diode (HBG 5566X, Stanley Electric, $\lambda_{max}$=555 nanometers, driven at 20 milliamps) is transmitted through the liquid film. The transmitted light is measured by a silicon photodiode and a detector. FIG. 4 shows the results.

EXAMPLE 2

The apparatus shown in FIGS. 1 and 3 is used to practice the instant invention. The collection reagent 23 is 1.0 millimolar $H_2SO_4$. A droplet having a diameter of about 2.0 millimeters is formed by pumping the collection reagent through the reagent supply capillary 54 which has an internal diameter of about 150 micrometers.

The resulting fluid is air that contains 250 parts per billion by volume ammonia ($NH_3$) as the component of interest. The fluid is fed to the collection/analysis chamber so that the fluid contacts the suspended droplet at a flow rate of about 0.12 liters per minute.

After sampling, the droplet is withdrawn into a sequential injection analysis system wherein sodium hypochlorite and sodium salicylate are sequentially reacted with the ammonia-bearing drop in the presence of alkaline nitroprusside as a catalyst. Indophenol blue is formed and the absorbance is measured at 630 nanometers using a linear PHD detector (Thermo Separation Products).

What is claimed is:

1. A method for determining a component of interest in a fluid, the method comprising the steps of:
    a) suspending a droplet of a liquid, wherein the liquid is immiscible with the fluid;
    b) contacting the fluid with the droplet;
    c) diffusing at least a portion of the component of interest into the droplet to form an analyte; and
    d) determining the component of interest by analyzing the analyte.

2. The method of claim 1, wherein the fluid is a gas.

3. The method of claim 1, wherein the fluid is a liquid.

4. The method of claim 2, wherein in step (d) the analyte is in the form of a suspended droplet.

5. The method of claim 3, wherein in step (d) the analyte is in the form of a suspended droplet.

6. A method for determining a component of interest in a fluid, the method comprising the steps of:

a) suspending a film of a liquid, wherein the liquid is immiscible with the fluid;

b) contacting the fluid with the droplet;

c) diffusing at least a portion of the component of interest into the droplet to form an analyte; and d) determining the component of interest by analyzing the analyte.

7. The method of claim 6, wherein the fluid is a gas.

8. The method of claim 7, wherein the fluid is a liquid.

9. The method of claim 7, wherein in step (d) the analyte is in the form of a suspended film.

10. The method of claim 8, wherein in step (d) the analyte is in the form of a suspended film.

* * * * *